United States Patent
Tam

(10) Patent No.: US 6,233,303 B1
(45) Date of Patent: May 15, 2001

(54) METHOD AND APPARATUS FOR REDUCING X-RAY DOSAGE IN A SPIRAL SCAN CONE BEAM CT IMAGING SYSTEM

(75) Inventor: Kwok Tam, Edison, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 09/358,071

(22) Filed: Jul. 21, 1999

(51) Int. Cl.[7] ....................................... A61B 6/03
(52) U.S. Cl. .................. 378/4; 378/15; 378/901
(58) Field of Search .................. 378/4, 8, 15, 901

(56) References Cited

U.S. PATENT DOCUMENTS

| | | | |
|---|---|---|---|
| 4,190,773 | 2/1980 | Braden et al. | 250/445 T |
| 5,504,792 | 4/1996 | Tam | 378/15 |
| 5,689,544 | 11/1997 | Van Den Besselaar | 378/150 |
| 5,878,103 | * 3/1999 | Sauer et al. | 378/15 |
| 5,881,123 | 3/1999 | Tam | 378/4 |
| 6,078,638 | * 6/2000 | Sauer et al. | 378/4 |

OTHER PUBLICATIONS

U.S. Application No. 09/052,415 filed Mar. 31, 1998 entitled "Practical Cone Beam Image Reconstruction Using Local Regions–of–Interest".

U.S. Application No. 09/343,770 filed Jun. 30, 1999 entitled "Exact Region of Interest Cone Beam Imaging Without Circle Scans".

* cited by examiner

Primary Examiner—David V. Bruce
(74) Attorney, Agent, or Firm—Donald B. Paschburg

(57) ABSTRACT

A scanning and data acquisition method and apparatus for three dimensional (3D) computerized tomography (CT) imaging of an ROI in an object, wherein a reconstructed image is developed by calculating reconstruction data along a plurality of line segments L formed in cone beam data acquired on a detector at a plurality of source positions about the ROI. The endpoints of the line segments L formed in the cone beam data acquired at each of the source positions is determined by a data combination mask which is applied to the cone beam data. When acquiring cone beam data near the top or bottom edges of the ROI, a radiation blocking element is operated for blocking radiation directed toward the ROI, so that only that portion of the detector is exposed to radiation.

16 Claims, 4 Drawing Sheets

METHOD AND APPARATUS FOR REDUCING X-RAY DOSAGE IN A SPIRAL SCAN CONE BEAM CT IMAGING SYSTEM

CROSS-REFERENCE TO RELATED APPLICATION

This application is related to U.S. patent application Ser. No. 09/343,770 filed Jun. 30, 1999, and it's parent U.S. patent application Ser. No. 09/274,189 filed Mar. 22, 1999.

BACKGROUND OF THE INVENTION

1. Field of the Invention

The invention relates generally to exact image reconstruction in a cone beam computed tomography (CT) imaging system, and more specifically to a method and apparatus for reducing radiation exposure to the object being imaged.

2. Description of the Prior Art

Recently a system employing cone beam geometry has been developed for three-dimensional (3D) computed tomography (CT) imaging that includes a cone beam x-ray source and a 2D area detector. An object to be imaged is scanned, preferably over a 360° angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions.

As well known, and fully described for example in the present inventor's U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, incorporated by reference herein, image reconstruction processing generally begins by calculating Radon derivative data from the acquired cone beam data. The Radon derivative data is typically determined by calculating line integrals for a plurality of line segments L drawn in the acquired cone beam data. In the embodiment described in detail in the '183 patent, Radon space driven conversion of the derivative data is used to develop an exact image reconstruction of a region of interest (ROI) in the object.

A cone beam data masking technique which improves the efficiency of the calculation of the Radon derivative data in such a Radon space driven technique is described in the present inventor's U.S. Pat. No. 5,504,792 entitled METHOD AND SYSTEM FOR MASKING CONE BEAM PROJECTION DATA GENERATED FROM EITHER A REGION OF INTEREST HELICAL SCAN OR A HELICAL SCAN, issued Apr. 2, 1996, and incorporated by reference herein. The masking technique facilitates efficient 3D CT imaging when only the ROI in the object is to be imaged, as is normally the case. In the preferred embodiment described therein, a scanning trajectory is provided about the object, the trajectory including first and second scanning circles positioned proximate the top and bottom edges, respectively, of the ROI, and a helical scanning path is connected therebetween. The scanning trajectory is then sampled at a plurality of source positions where cone beam energy is emitted toward the ROI. After passing through the ROI, the residual energy at each of the source positions is acquired on a detector as a given one of a plurality of sets of cone beam projection data. Each set of the cone beam projection data is then masked so as to remove a portion of the cone beam projection data that is outside a given sub-section of a projection of the ROI in the object and to retain cone beam projection data that is within the given sub-section. The masked cone beam projection data is then processed so as to develop reconstruction data, and an exact image of the ROI is developed by combining the reconstruction data. Hence, the masks are commonly referred to as "datacombination" masks.

Data-combination masks can also be used to improve the efficiency of the calculation of the derivative data in a detector data driven technique, such as the 3D backprojection technique described in the present inventor's U.S. Pat. No. 5,881,123 entitled SIMPLIFIED CONE BEAM IMAGE RECONSTRUCTION USING 3D BACKPROJECTION, issued Mar. 9, 1999, also incorporated herein by reference.

The present inventor's U.S. patent application Ser. No. 09/274,189 entitled EXACT REGION OF INTEREST CONE BEAM WITHOUT CIRCLE SCANS, filed Mar. 22, 1999, incorporated by reference herein, improved upon the invention described in the forenoted U.S. Pat. No. 5,504,792, by providing an exact image reconstruction of an ROI in an object without the requirement that the source scan path have top and bottom circle scan path trajectories proximate the top and bottom edges of the ROI. Furthermore, the improvement is applicable to both of the Radon space and detector driven types of image reconstruction processing. As described in this U.S. patent application Ser. No. 09/274,189, and consistent with the techniques described in the above noted U.S. Pat. Nos. 5,881,123 and 5,504,792, when calculating the derivative data, the length of the line segments L formed in the acquired cone beam data are determined by the boundaries of the data combination mask. However, when processing line segments L formed in cone beam data acquired at source positions near the top or bottom edges of the ROI, groups of the line segments L have one of their end points determined by a horizontal line (the x-axis) of the mask. Acquired cone beam data which resides on one side of the horizontal axis of the mask is not used. Thereafter, integral data calculated for the line segments L formed in the masked cone beam data are processed so as to develop contribution to a 3D image reconstruction of the ROI in the object. Since some of the acquired projection data is not used, some of the radiation exposure suffered by the object is unnecessary. This is undesirable, especially if the object is a human being.

It would be desirable to provide a method and apparatus for exact image reconstruction processing which makes more efficient use of the X-ray dose applied to the object being imaged.

SUMMARY OF THE INVENTION

In accordance with the principles of the present invention, during image reconstruction, line segments L formed in cone beam projection data acquired at source positions near the top or bottom edges of the ROI have one of their end points determined by a horizontal line through the mask. Thus, acquired cone beam projection data which resides on one side of the horizontal line in the mask is not used for image reconstruction processing. Accordingly, a radiation blocking element, or shutter, is provided between the radiation emitting source and the object being imaged, and operated at source positions near the top or bottom edges of the ROI so as to block a portion of the radiation directed toward the ROI. In a preferred embodiment of the invention, the blocked portion is that radiation which would contribute to the cone beam projection data which resides on the one side of the horizontal line in the mask.

DETAILED DESCRIPTION OF THE INVENTION

Figure 1:
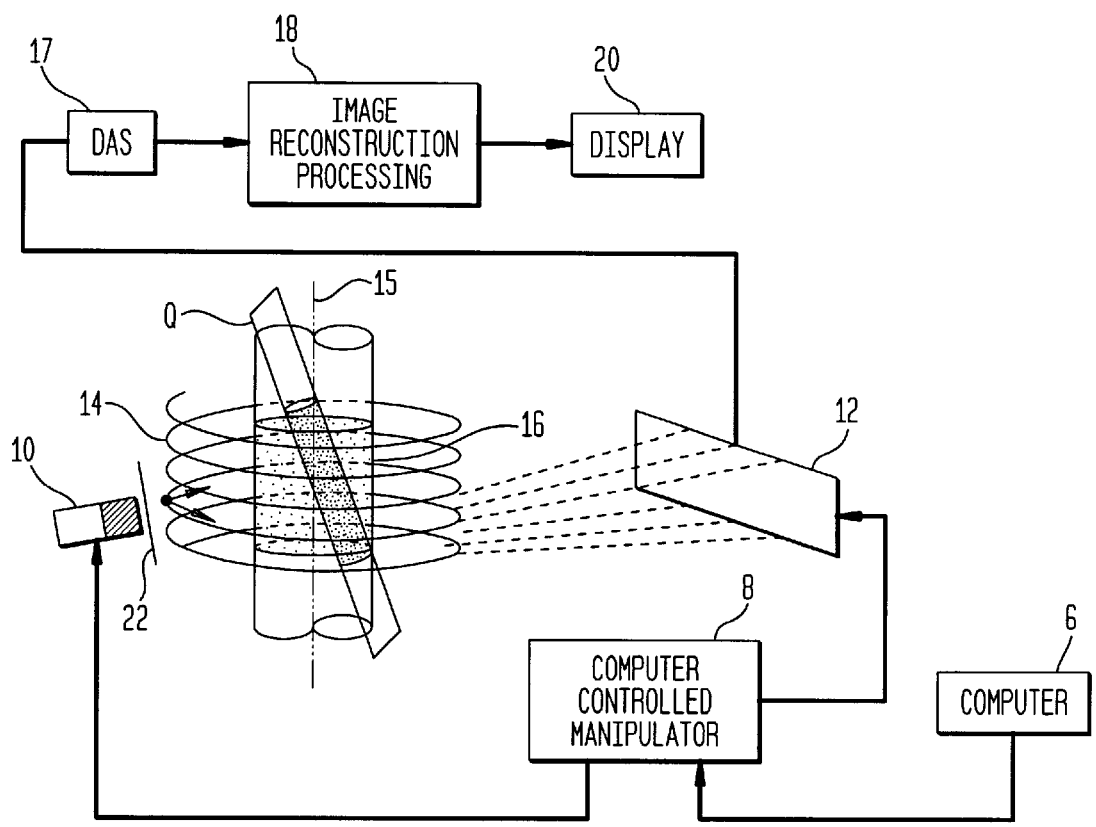
FIG. 1 illustrates a 3D CT imaging apparatus having a shuttered cone beam x-ray source, useful for acquiring and processing cone beam data in accordance with the principles of the present invention.

FIG. 1 illustrates a cone beam 3D CT imaging apparatus useful for acquiring and processing acquired cone beam data in accordance with the principles of the present invention. The illustrated imaging apparatus is constructed and operates substantially in accordance with same principles described in the forenoted U.S. Pat. No. 5,257,183 and using image reconstruction techniques as described in the forenoted U.S. patent application Ser. No. 09/052,281, already incorporated herein by reference, except that image reconstruction processing in accordance with the present invention is accomplished in conjunction with a radiation blocking shutter for blocking radiation exposure to a portion of the object at source positions near the top and bottom edges of the ROI, as will be more specifically described.

As shown in FIG. 1, a computer controlled manipulator 8, in response to control signals from an appropriately programmed computer 6, cause a source 10 of a cone or pyramid shaped beam of energy (such as x-rays) and a twodimensional pixelated detector array 12 to cooperate (scan) at a plurality of discreet, sequentially occurring adjacent source positions, along a pre-defined source scanning path. In the illustrated embodiment the scanning path is shown as a spiral scan path 14 centered on a predetermined axis 15 of an object 16, and which proceeds in a counterclockwise direction. Other types of scan paths that encircle and traverse object 16 can also be used, however, a scan path 14 exhibiting a high degree of symmetry in its parallel projection is preferred.

The only height requirement on the detector is that it should be more than the distance between adjacent turns of a cone beam projection of the spiral scan path 14 onto the detector 12. As described in the forenoted U.S. patent application Ser. No. 09/274,189, when only an ROI (shaded area) of object 16 is to be imaged, providing top and bottom scan path circles at the top and bottom ends, respectively, of the ROI, are not necessary. Thus, a simple continuous spiral scan path 14 that traverses the length of the ROI is all that is needed.

As a result of the source/detector cooperation under control of computer 6 and manipulator 8, at each of the source positions, beams of x-ray energy pass through the field of view of the imaging apparatus, are selectively attenuated by varying energy absorbing densities inside object 16, and a set of cone beam data corresponding to the sensed x-ray energy falling on the elements (pixels) of detector 12 are developed. The sets of cone beam data are then supplied to a data acquisition system (DAS) 17 which, like the previously described portions of FIG. 1, may operate in a fashion well known to those of ordinary skill in this technology for digitizing and storing of the acquired cone beam data.

As described in the present inventor's forenoted U.S. Pat. No. 5,257,183, image reconstruction processing 18 begins by calculating derivative data from the acquired cone beam data, such data being calculated for those portions of integration planes Q which intersect both the scan path and the ROI. One such Q-plane is shown in FIG. 1. As described in detail in the forenoted U.S. Pat. No. 5,257,183, Radon space driven conversion of the derivative data is used to develop an image reconstruction of object 16 on a display 20. The forenoted U.S. Pat. No. 5,504,792 describes the use of data combination masks to improve the efficiency of the calculation of the derivative data in such a Radon space driven technique. Alternatively, as will become apparent later, image reconstruction processing 18 of the present invention can also be a detector data driven technique, such as the 3D backprojection technique described in the forenoted U.S. patent application Ser. No. 09/052,281. In either case, however, in accordance with the principles of the present invention, the imaging apparatus modified so as to include a radiation blocking element or shutter 22, as described in greater detail below, which is selectively operated so as to reduce the radiation dose directed toward the object being imaged.

In order to more fully understand the principles of the present invention, some review of the previously noted U.S. patent application Ser. No. 09/274,189 will be provided. As was noted above, this technique for ROI imaging does not have the requirement that the imaging apparatus provide circle scans even with the top and bottom ends of the ROI. This is accomplished by processing the acquired cone beam data using a "local 2D ROI" approach, as was first described in the present inventor's U.S. patent application Ser. No. 09/052,415 entitled PRACTICAL CONE BEAM IMAGE RECONSTRUCTION USING LOCAL REGIONS-OF-INTEREST, filed Mar. 31, 1998, incorporated herein by reference, wherein specific sub-sets of Radon space data are developed. Each of the sub-sets of Radon space data is targeted for reconstructing a corresponding sub-section or "local" portion of a 2D ROI. Each local ROI is a 2D parallel projection of the ROI in the object on an individual one of the plurality of vertically oriented coaxial φ-planes that partition the Radon space. Due to the nature of a parallel projection, the upper and lower bounds of the local 2D ROI projection images do not suffer data corruption from x-rays emitted from the source which pass through areas outside the bounds of the local ROI. When a sufficient number of these local 2D ROI projection images are developed over 180 degrees (the sufficiency being determined by the desired resolution of the final image reconstruction), they are processed, using Radon inversion techniques, for directly developing contributions to the final image reconstruction, thereby obviating the requirement to provide circle scans at the top and bottom ends of the ROI.

In the forenoted U.S. patent application Ser. No. 09/274,189 these image reconstruction techniques are further simplified and also extended for use in a detector data driven image reconstruction arrangement, such as Filtered Backprojection, (FBP). The arrangement of the present invention is useful in conjunction with either one of these two image reconstruction techniques, however, for brevity, only its use in conjunction with the FBP approach will be described.

Figure 2A:
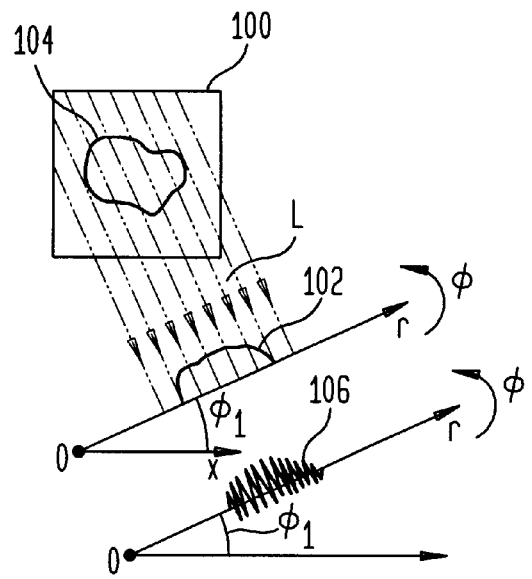
FIGS. 2A and 2B illustrate a 3D backprojection approach for reconstructing an image using the apparatus of FIG. 1.
Figure 2B:
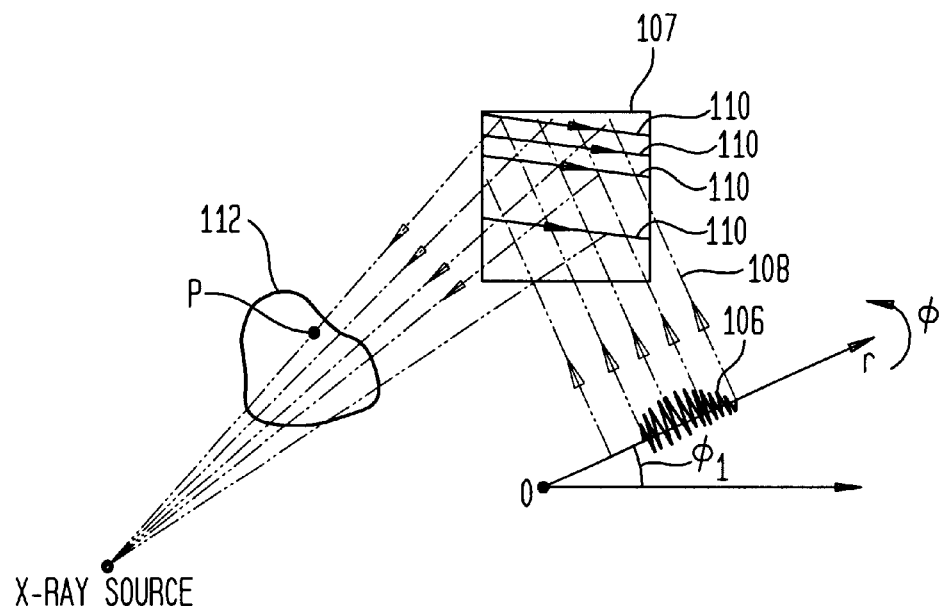
Figure 3A:
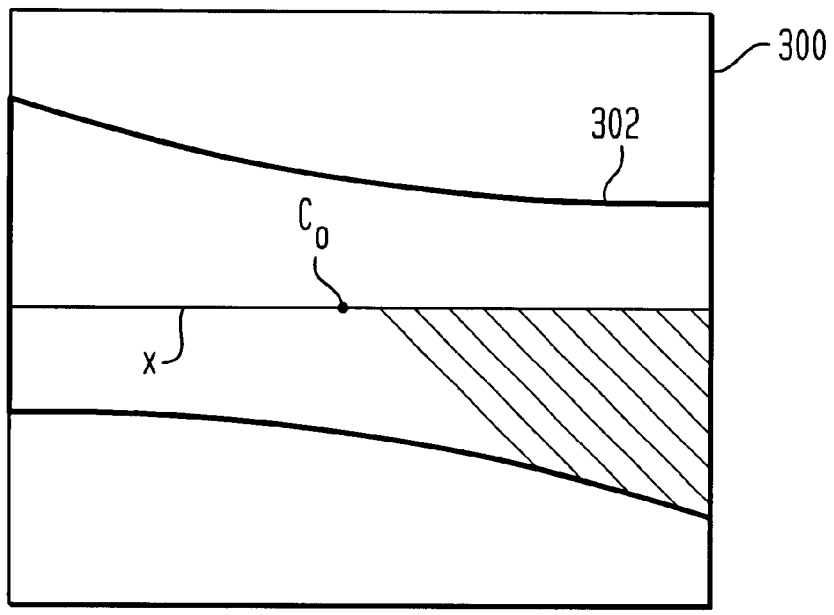
FIGS. 3A and 3B illustrate masking of lines formed on the sets of cone beam data acquired near the top edge of an ROI in an object, for use to reconstruct and image in accordance with the invention.
Figure 3B:
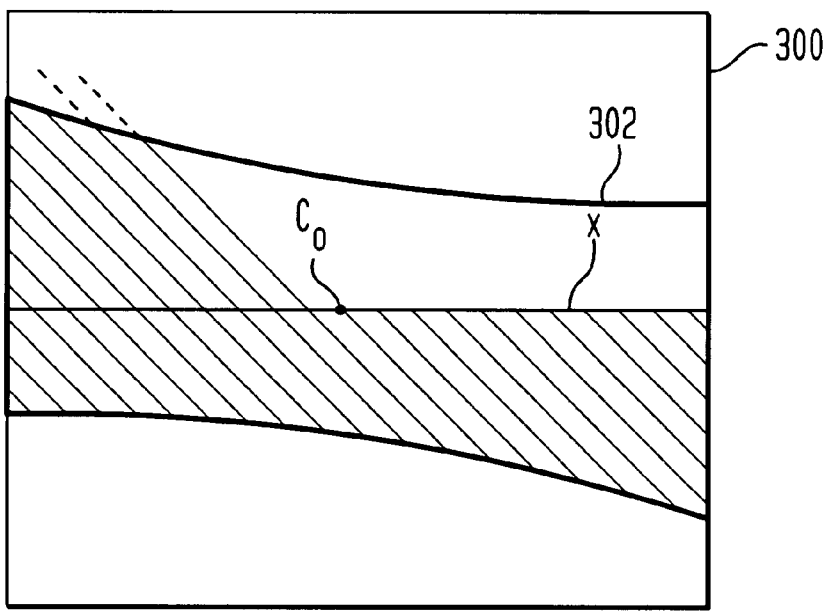

FBP image reconstruction consists of two steps: the first is a 2D step and the second is a 3D step. In the first step, each cone beam projection image is processed in a 2D space, and in the second step, the processed image is backprojected into a 3D object space. As shown in FIGS. 2A and 2B, the 2D step consists of the following 4 sub-steps for processing the cone beam data acquired at each of a plurality of the source positions ($S_i$) along the scan path:

1. Compute a 1D projection (i.e., a line integral) of the cone beam image acquired on a detector plane 100, at each of a plurality of angles θ. This step is illustrated in FIG. 2A for a given angle $θ_1$ of a plurality of angles θ. A 1D projection 102 is shown at coordinates r, $θ_1$ comprising the integrated values of the cone beam image 104 on detector plane 100 along a plurality of parallel lines L(r, θ) that are normal to angle$θ_1$, each line L being at an incremental distance r from an origin O. As shown and described below in conjunction with FIGS. 3A and 3B illustrating processing of cone beam data acquired near the top edge of the ROI, the lengths of the lines L will be limited using the forenoted data-combination masking techniques. Generally, if the detector plane 100 comprises an N by N array of pixels, then the number of angles θ is typically given by πN/2.

2. Filter (differentiate) each 1D projection 102 in accordance with a d/dr filter, resulting in a new set of values at each of the r, θ coordinates, such as shown by the derivative projection 106 for the angle $θ_1$ shown in FIG. 2A. Note, the sum of the resulting values at these r, θ coordinates yield a quantity proportional to the Radon derivative for the integration plane Q(r, θ), as described above for Radon space driven image reconstruction processing.

3. As illustrated by FIG. 2B, backproject the derivative projection 106 from each angle θ into a 2D object space 107 (which coincides with the detector plane 100). Lines 108 are representative of this backprojection, and spread the value from each r coordinate into the 2D space 107 in a direction normal to each θ. Note, 2D object space 107 has a size corresponding to a virtual detector which is enlarged (compared with detector 12 of FIG. 1), so as to cover the entire ROI in the object. This enlargement is required because the calculated Radon data affects the reconstruction of the entire Q plane, and not just the partial plane represented by the data combination mask.

4. Perform a 1D d/dt filtering of the backprojection image formed in 2D space 107 by step 3. The 1D filtering is performed in the direction of the scan path, i.e., along lines 110, where t points in the direction of the projection of a line drawn tangent to the scan path.

As shown in FIG. 2B, the 3D step comprises performing a weighted 3D backprojection of the resulting data from 2D space 107 (i.e., from each pixel in the detector) onto a plurality of sample points P in a 3D object volume 112. The density assigned to each point P is weighted by the inverse of the square of the distance between the sample point and the location of the x-ray.

Figure 4:
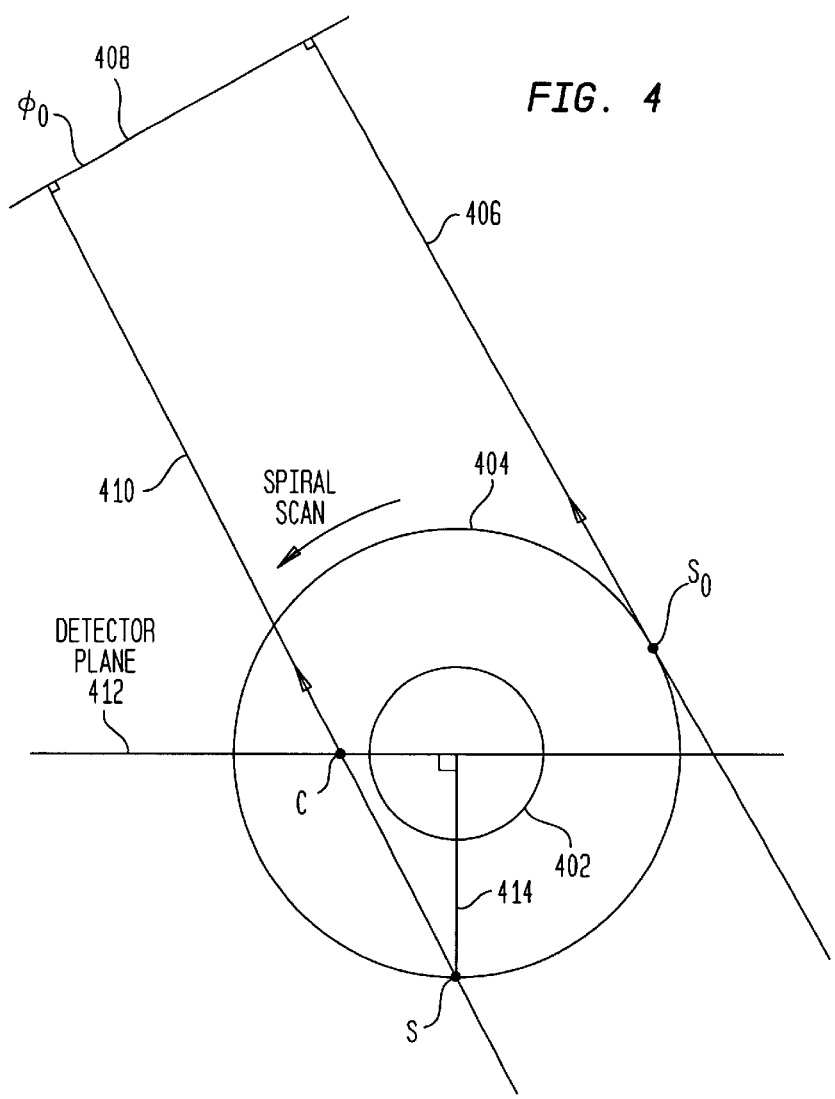
FIG. 4 illustrates a top view of a portion of the image reconstruction geometry used to determine the point $C_o$ in the masks shown in FIGS. 3A and 3B.

Application of a data-combination mask to processing of the acquired cone beam data when reconstructing an image using either the FBP or Radon inversion image reconstruction techniques for source positions which are internal to the top and bottom 2π angular range of the scan path about the ROI, use the data-combination masking technique such as known from the forenoted U.S. Pat. No. 5,504,792. However, when reconstructing an image from data acquired at source positions which are at the top and bottom 2π angular range of the scan path about the ROI, the techniques shown in FIGS. 3A and 3B are used. As shown, in a set of cone beam data 300 acquired at a given source position $S_i$, a point $C_0$ is marked on the x-axis of the detector. The technique for marking the point $C_0$ is described in detail in the forenoted U.S. patent application Ser. No. 09/052,281, and described more briefly below in conjunction with FIG. 4. Next, an appropriate data combination mask 302 is applied to the cone beam data, and a plurality of lines L are formed in each set 300 of the acquired cone beam data in accordance with Step 1 of FIG. 2A. The endpoints (and hence the length) of the line segments L are determined by the outer boundaries of the data combination mask for all source positions that are between the top and bottom 2π angular range in the scan path that are near the top and bottom edges, respectively, of the ROI. However, at source positions in the top and bottom π angular range (i.e., the outermost or first turns) in the scan path, the endpoints for the line segments drawn in the acquired cone beam data are determined by one boundary and the horizontal axis of the data combination mask, as shown in FIGS. 3A and 3B. That is, all line segments L which cross the horizontal axis to one side of a point $C_0$ (which point is determined as shown in FIG. 4), have their endpoints determined by one of the upper or lower boundaries of the mask and its horizontal (i.e., x) axis, and all of those line segments crossing the horizontal axis to the other side of $C_0$, are either not used, or are determined by outer boundaries of the data combination mask. (Note, in the illustrated embodiment the x-axis of the data combination mask is coincident with the x-axis of the detector, but such coincidence is not required.)

More specifically, FIG. 3A illustrates masking for data acquired at a source position in the first (or outer) π angular range of the scan path near the top of the ROI, and as shown therein the unused cone beam data is that data where the lines L cross the x-axis to the left of point $C_0$, as well as all the data above the x-axis. If the source position which acquired the data was near the bottom of the ROI, the image of FIG. 3A would be turned upside down and reversed, i.e., the unused data would be where the lines L cross the x-axis to the right side of the point $C_0$, as well as all the data below the x-axis.

At source positions in the second (or inner) π angular range near the top and bottom of the scan path, the endpoints for line segments L which cross the horizontal axis to one side of point $C_0$ have their endpoints determined by one of the upper or lower boundaries of the mask and its horizontal axis, and all of those line segments crossing the horizontal axis to the other side of $C_0$ have their endpoints determined by both of the upper and lower boundaries of the mask. FIG. 3B illustrates this for a source position in the second (or next inner) π angular range near the top of the scan path. If the source position which acquired the data was near the bottom of the ROI, the image of FIG. 3B would also be turned upside down and reversed. Here we have assumed the spiral scanning motion is right-handed with the spiral axis pointing in the +y direction; the analysis can easily be modified to accommodate other scanning configurations.

The following analysis, in conjunction with FIG. 4, describes how to determine the point $C_0$ in the data acquired at any source position $S_i$, starting from and including a starting source position $S_0$. FIG. 4 illustrates a top view of a portion of the image reconstruction geometry, wherein a circle 402 is representative of the object and a circle 404 is representative of the spiral path traversed by the x-ray source S (shown as 10 in FIG. 1). The starting source position $S_0$ is marked on scan path circle 404. As previously described, in order to provide an exact image reconstruction and avoid image artifacts, a parallel projection of the scan path must, at a minimum, begin and end outside of the local ROI of the object. Accordingly, a line 406 is drawn starting from source position $S_0$ so as to be tangential to circle 404

(i.e., touching the outside edge of scan path 14). The Radon space φ-plane which forms an orthogonal intersection with line 406 defines the Radon space $\phi_0$-plane, which is labeled 408.

Then, assuming an anti-clockwise rotation of the source S, mark a source position $S_i$ on scan path circle 404. Next, one draws a line 410 which passes through source position $S_i$ and is parallel with line 406, and therefore also bears an orthogonal relationship to the Radon space $\phi_0$-plane 408. Then, $C_0$ is defined as that point on the x-axis in the detector plane that acquires the cone beam data at source position $S_i$, which is intersected by line 410. (Note, the detector plane that acquired the cone beam data at source position $S_i$, i.e., detector plane 412, is determined by its orthogonal relationship to a line 414, which is drawn from source position $S_i$ to the center of object circle 402.) This $C_0$ is used, as noted above, to group the line segments formed in the cone beam data during image reconstruction processing, in accordance with the manner of their length limitation. In this manner, the location of $C_0$ for all of the source positions S can be determined. (The anti-clockwise rotation assumed in the above analysis can be easily modified for the opposite sense of source rotation.)

However, as evidenced by FIG. 3A for a source position in the first π angular range of the scan path near the top of the ROI (or its revered and inverted image for source positions in the first π angular range of the scan path near the bottom of the ROI), there are source positions in this technique wherein radiation is directed to the object and the cone beam projection data acquired which resides on one side of the horizontal line in the mask is not used for image reconstruction.

In accordance with the principles of the present invention, a radiation blocking element, or shutter, is provided between the radiation emitting source and the object being imaged, and operated at source positions near the top or bottom edges of the ROI so as to block that portion of the radiation directed toward the ROI which contributes to the acquisition of unused cone beam projection data.

More specifically, as shown in FIG. 1, a radiation blocking element, or shutter, 22, is provided between the x-ray source 10 and the object 16, for selectively blocking radiation directed toward the object.

In operation, during the first π angular range of the spiral scan (i.e., near the top edge of the ROI), an upper part 22a of shutter 22 is deployed to block off the upper half of the x-ray cone beam, and during the last π angular range of the spiral scan (i.e., the turn near the bottom edge of the ROI), a lower part 22b of shutter 22 is deployed to block off the lower half of the x-ray cone beam.

Figure 5:
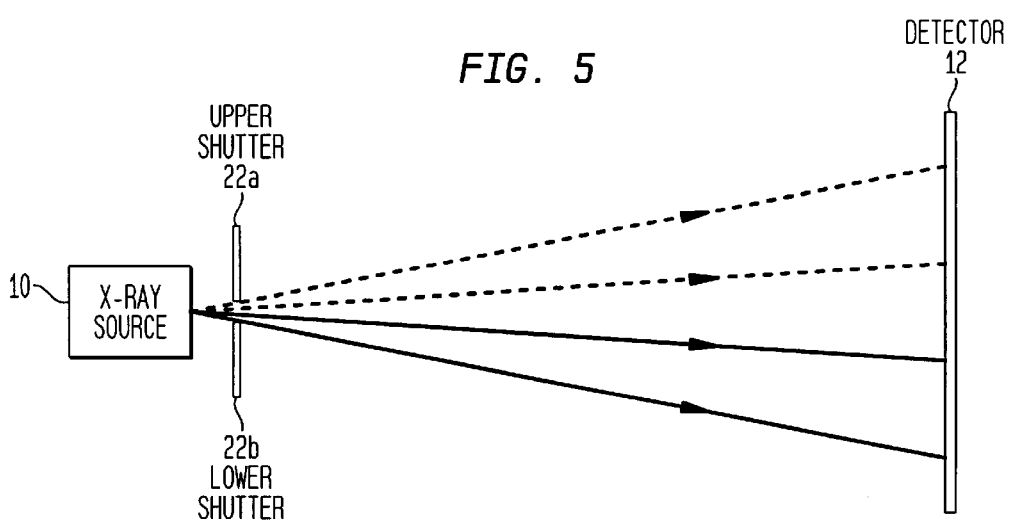
FIG. 5 illustrates the operation of the shutter portion of the apparatus of FIG. 1.

One way to implement the invention is shown in FIG. 5. There are two shutters (22a and 22b) in front of x-ray source 10. When the spiral scan starts, shutter 22a is in place to block radiation from reaching the top half of detector 200, while bottom shutter 22b is out of place. As a result the top half of the x-ray cone beam is completely blocked off. When the source enters the next π angular range of the scan path, the shutter 22a is lifted and the entire x-ray cone beam is used to expose the object, and the detector. When the scan reaches the last π angular range of the scan path, shutter 22b is put into place to block off the lower half of the x-ray cone beam. The above described operation of shutter 22 results from control signals (not specifically shown) applied thereto from the computer 6. Details exactly describing the mechanical linkages and control mechanisms for shutter 22 are not described herein since they are within the knowledge of those of ordinary skill in this technology, and may be constructed as known in prior patent documents, such as U.S. Pat. No. 4,190,773.

In accordance with the principles of the invention, the radiation dose exposure to the object during the first and last π angular ranges of the scan path near the top and/or the bottom of the ROI is able to be reduced by 50%. This reduction in radiation dosage as a percentage of the total radiation dose delivered to the object increases as the spiral pitch increases, because a longer spiral pitch reduces the number of interior spiral turns required to span a given length of the object. Since the spiral pitch can increase as the height of the detector increases, and the trend in cone beam CT systems is to develop longer and longer detectors in order to increase scanning speed, the reduction in radiation dosage made possible by this invention will become more and more significant, (e.g., up to about a 30% of the entire dose is possible).

Thus, there has been shown and described a novel 3D CT imaging method and apparatus for obtaining an exact image reconstruction which makes more efficient use of the X-ray dose applied to the object being imaged. Many changes, modifications, variations and other uses and applications of the subject invention will, however, become apparent to those skilled in the art after considering this specification and its accompanying drawings, which disclose a preferred embodiment thereof For example, as previously noted, the invention can be used in either of the Radon space driven or detector driven image reconstruction types of processing. Furthermore, although in the preferred embodiment the x-axis of the detector was coincident with the x-axis of the data-combination masks, such coincidence is not required, nor is it required to provide a complete blocking of the radiation exposure to one side of the axis (even a partial blocking of the radiation to one side of the axis would be desirable). Even furthermore, the exact details concerning the construction and operation of the shutter can be modified to accommodate other changes in the imaging apparatus and its methods of operation, and the scan path could have non-uniform pitch and/or other variations. Additionally, although in the preferred embodiment the shutter is operated to reduce radiation dose at both of the top and bottom edges of the ROI, its operation at only one such edge of the ROI would also be useful. Finally, it is noted that although in the illustrated embodiment it is preferred that shutter 22 block 100% of the radiation directed to a predetermined portion of the detector when it is operated, it is possible to still obtain an advantageous reduction in radiation dosage in accordance with the principles of the present invention if in an alternative embodiment shutter 22 was less than 100% effective in blocking such directed radiation. All such changes, modifications, variations and other uses and applications which do not depart from the teachings herein are deemed to be covered by this patent, which is limited only by the claims which follow as interpreted in light of the foregoing description.

What is claimed is:

1. Apparatus for performing three dimensional computerized tomographic imaging of a region-of-interest (ROI) in an object using a cone beam source of radiation energy, comprising:

a source of cone beam radiation energy;

a manipulator for providing a source scanning trajectory as a scan path that encircles the ROI in the object and causes an area detector and the source to traverse the scan path;

a controller coupled to the manipulator and the source for causing the source to apply radiation energy towards the object from a plurality of source positions along the scan path as the source traverses the scan path, the area detector acquiring cone beam projection data corresponding to respective portions of the object at each of said source positions;

an image reconstruction processor for applying a mask to the cone beam projection data acquired by the area detector at each of the source positions, and calculating therefrom reconstruction data along each of a plurality of line segments L formed in the masked cone beam projection data;

a radiation blocking element responsive to the controller for selectively blocking radiation directed toward the object so as to expose only a sub-portion of the area detector; and a reconstruction processor for processing said reconstruction data for reconstructing a 3D image of the ROI in the object.

2. The apparatus of claim 1, wherein the controller causes said radiation blocking element to block radiation from reaching the sub-portion of the detector when the detector is acquiring cone beam data at source positions along first and second portions of the scan path.

3. The apparatus of claim 2, wherein said first and second portions of the scan path correspond to a π portion of the angular range of the scan path near a top and bottom edge, respectively, of the ROI.

4. The apparatus of claim 1, wherein:

the mask applied to the cone beam projection data by the image reconstruction processor has upper and lower boundaries formed by cone beam projections onto the plane of the detector of portions of the source scan path that are above and below, respectively, the source position that acquired the data being masked, as well as a horizontal axis; and the radiation blocking element blocks radiation directed toward the object so as to not expose a portion of the detector which resides on one side of the horizontal axis of the mask.

5. The apparatus of claim 4, wherein the controller causes said radiation blocking element to block radiation from reaching that portion of the detector which resides on an upper side of horizontal axis in the mask when the detector is acquiring cone beam data at source positions along a first portion of the scan path.

6. The apparatus of claim 5, wherein the controller causes said radiation blocking element to block radiation from reaching that portion of the detector which resides on a lower side of the horizontal axis in the mask when the detector is acquiring cone beam data during a second portion of the scan path.

7. The apparatus of claim 5, wherein said first portion of the scan path corresponds to a π portion of the angular range of the scan path near a top edge of the ROI.

8. The apparatus of claim 6, wherein said second portion of the scan path corresponds to a π portion of the angular range of the scan path near the bottom edge of the ROI.

9. A method for performing three dimensional computerized tomographic imaging of a region-of-interest (ROI) in an object using a cone beam source of radiation energy, comprising the steps of:

defining a source scanning trajectory as a scan path that encircles the ROI in the object and is traversed by the cone beam source;

using the cone beam source, fixed relative to an area detector with both source and detector movably positioned relative to the object, for applying radiation energy towards the object from a plurality of source positions along the scan path as said source traverses the scan path, said applying causing said area detector to acquire cone beam projection data corresponding to respective portions of the object at each of said source positions;

masking the cone beam projection data acquired at each of said source positions with a mask;

calculating reconstruction data from each of a plurality of line segments L formed in the masked cone beam projection data acquired at each of said source positions, said mask being used during said calculating step to determine the length of the line segments L formed therein;

selectively blocking radiation directed toward the object so as to expose only a sub-portion of the area detector corresponding substantially to the length of the line segments L formed in the masked cone beam projection data acquired at each of said source positions; and reconstruction processing the reconstruction data calculated for said line segments L, for reconstructing a 3D image of the ROI in the object.

10. The method of claim 9, wherein:

the mask applied to the cone beam projection data by the image reconstruction processor has upper and lower boundaries formed by cone beam projections onto the plane of the detector of portions of the source scan path that are above and below, respectively, the source position that acquired the data being masked, as well as a horizontal axis; and said selective radiation blocking blocks radiation directed toward the object so as to not expose a portion of the detector which resides on one side of the horizontal axis in the mask.

11. The method of claim 10, wherein said selective radiation blocking blocks radiation from reaching that portion of the detector which resides on an upper side of horizontal axis in the mask when the detector is acquiring cone beam data at source positions along a first portion of the scan path.

12. The method of claim 11, wherein said selective radiation blocking blocks radiation from reaching that portion of the detector which resides on a lower side of the horizontal axis in the mask when the detector is acquiring cone beam data during a second portion of the scan path.

13. The method of claim 11, wherein said first portion of the scan path corresponds to a π portion of the angular range of the scan path near a top edge of the ROI.

14. The method of claim 12, wherein said second portion of the scan path corresponds to a π portion of the angular range of the scan path near the bottom edge of the ROI.

15. The method of claim 9, wherein said selective radiation blocking blocks radiation from reaching the sub-portion of the detector when the detector acquires cone beam data at source positions along first and second portions of the scan path.

16. The method of claim 15, wherein said first and second portions of the scan path correspond to a π portion of the angular range of the scan path near a top and bottom edge, respectively, of the ROI.

* * * * *